United States Patent [19]

Amato et al.

[11] 4,071,572

[45] Jan. 31, 1978

[54] CYCLIC ETHYLENE OXYHYDROCHLORINATION PROCESS WITH REDUCED HYDROCARBON EMISSIONS

[75] Inventors: Wayne S. Amato, Syracuse; Bhaskar Bandyopadhyay, Camillus; Robert Herbert Fitch, Syracuse; Bruce Edward Kurtz, Marcellus, all of N.Y.

[73] Assignee: Allied Chemical Corporation, Morris Township, N.J.

[21] Appl. No.: 587,781

[22] Filed: June 17, 1975

[51] Int. Cl.$^2$ .............................................. C07C 17/02
[52] U.S. Cl. ................................................ 260/659 A
[58] Field of Search ........... 260/659 A, 656 R, 658 R, 260/662 A

[56] References Cited

U.S. PATENT DOCUMENTS

| 2,498,546 | 2/1950 | Gorin ................................ 260/659 A |
| 2,644,846 | 7/1953 | Johnson et al. ................... 260/659 A |
| 2,746,844 | 5/1956 | Johnson et al. ................. 260/659 A X |
| 2,952,714 | 9/1960 | Milam et al. ......................... 260/662 |
| 3,159,455 | 12/1964 | Skaperdas et al. ........... 260/659 A X |
| 3,341,612 | 9/1967 | Hayes et al. ...................... 260/659 A |
| 3,345,422 | 10/1967 | Piester et al. ................. 260/659 A X |
| 3,427,359 | 2/1969 | Rectenwald et al. ........... 260/659 A |
| 3,551,506 | 12/1970 | Weinstein .................... 260/659 A X |
| 3,637,895 | 1/1972 | Riegel et al. ................. 260/659 A X |
| 3,699,178 | 10/1972 | Suzuki et al. .................... 260/659 A |
| 3,892,816 | 7/1975 | Kister .............................. 260/659 A |

*Primary Examiner*—Floyd D. Higel
*Attorney, Agent, or Firm*—Anthony J. Stewart; Gerhard H. Fuchs

[57] ABSTRACT

A cyclic process having reduced hydrocarbon emission is provided for oxyhydrochlorination of ethylene to produce ethylene dichloride employing substantially pure oxygen as feed to the oxyhydrochlorination unit and recycling a major portion of the residual gas stream from which ethylene dichloride has been recovered as condensate, wherein reactant feed rates are adjusted to maintain recycle gas stream composition within specified limits.

7 Claims, 1 Drawing Figure

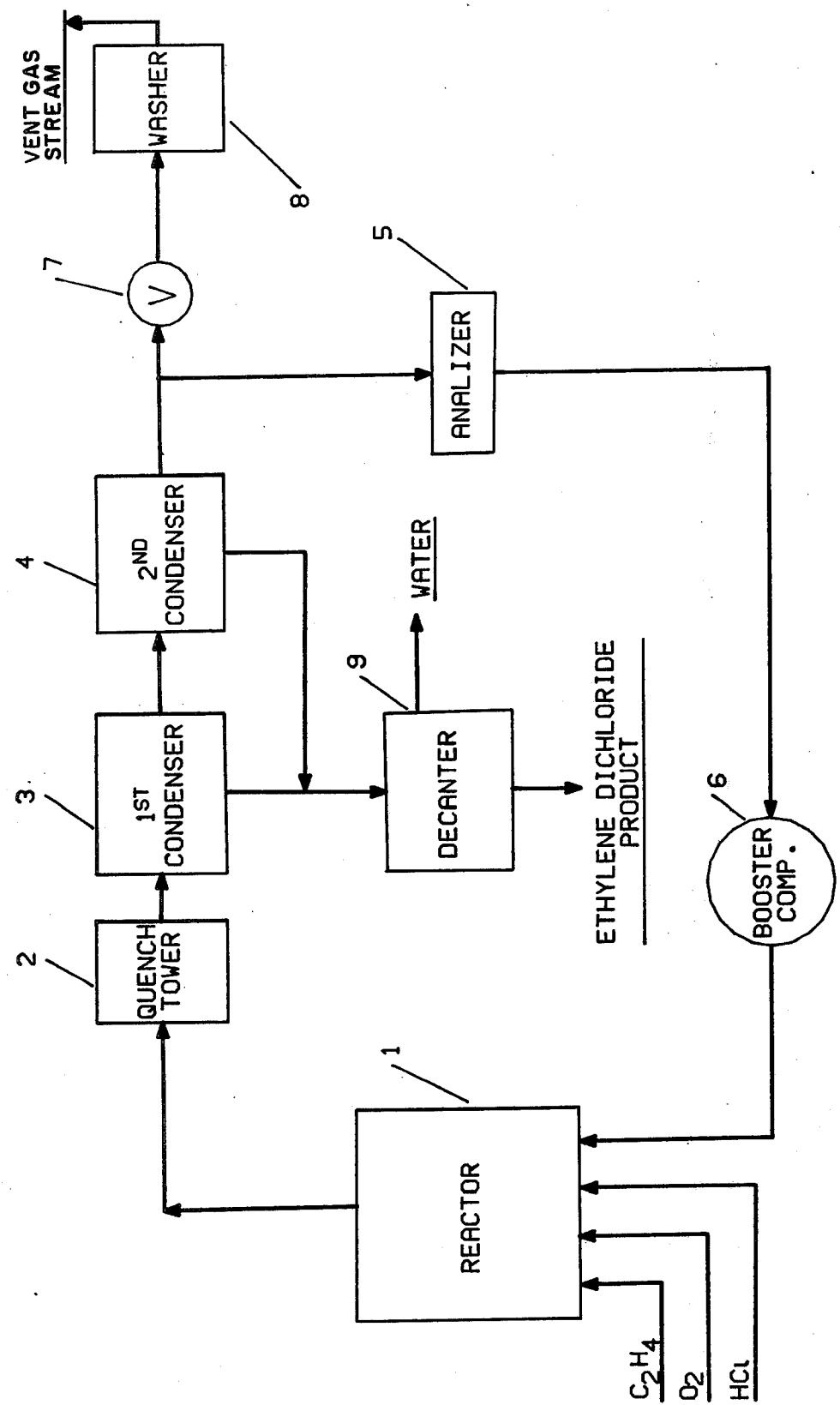

CYCLIC ETHYLENE OXYHYDROCHLORINATION PROCESS WITH REDUCED HYDROCARBON EMISSIONS

BACKGROUND OF THE INVENTION

The invention described herein was made in the course of, or under, a contract with the Environmental Protection Agency (Contract No. 68-02-1835.)

1. Field of the Invention

This invention relates generally to the production of ethylene dichloride by oxyhydrochlorination of ethylene, and provides the advantage of reduced hydrocarbon emissions therefrom.

2. Description of the Prior Art

Production of vinyl chloride is almost exclusively based on ethylene and usually involves three main steps:

direct chlorination of ethylene $$C_2H_4 + Cl_2 \rightarrow C_2H_4Cl_2;$$

oxyhydrochlorination of ethylene $$C_2H_4 + 2 HCl + \tfrac{1}{2} O_2 \rightarrow C_2H_4Cl_2 + H_2O;$$

and cracking of ethylene dichloride $$2 C_2H_4Cl_2 \rightarrow 2 C_2H_3Cl + 2 HCl.$$

The overall reaction in this balanced process is $$2 C_2H_4 + Cl_2 + \tfrac{1}{2} O_2 \rightarrow 2 C_2H_3Cl + H_2O.$$

The oxyhydrochlorination step is the technically most difficult part of the overall process, but it has had a profound impact on the industry since its development. The first commercial ethylene oxyhydrochlorination process appeared in 1964 and within the next few years the classical process for making vinyl chloride from acetylene was almost completely displaced by it.

In the ethylene oxyhydrochlorination step, ethylene, hydrogen chloride and air are introduced into a reaction zone containing Deacon-type catalyst where the oxyhydrochlorination reaction takes place. Downstream product recovery generally involves cooling of the reaction gases by either direct quench or heat exchanger, followed by condensation of the ethylene dichloride product and water by-product which are separated by decantation. Since the remaining gases still contain significant amounts of ethylene dichloride, they are further processed in a secondary recovery system employing solvent absorption and/or a refrigerated condenser. The off-gas is then vented to the atmosphere.

The vent stream contains mostly nitrogen from the air employed as source of oxygen for the oxyhydrochlorination reaction, but also includes a variety of other compounds which originate either in the feeds to the reactor or as by-products of the reaction, such as carbon dioxide and carbon monoxide formed by oxidation of ethylene; ethyl chloride formed from a side-reaction of ethylene with hydrogen chloride; methane which is an impurity in the ethylene feed passes through the reactor unaffected together with any unreacted ethane, also an impurity in the ethylene feed; ethylene dichloride which escapes from the secondary recovery system; solvent which escapes from the secondary recovery system; and ethylene and oxygen which remain unreacted.

This vent stream is the main source of hydrocarbon emissions associated with the manufacture of vinyl chloride. The direct chlorination process produces less than one-tenth of the hydrocarbon emissions of oxyhydrochlorination, and cracking of ethylene dichloride, under normal circumstances, produces no emissions. Ethylene dichloride production is stated to account for 28% of the hydrocarbon emissions in the United States in Southern Louisiana and East Texas.

There is no practical way of eliminating the oxyhydrochlorination vent from existing processes; the gases are too dilute for direct incineration and the addition of natural gas to make the gases combustible in an extravagance. Furthermore, incineration will form hydrochloric acid which must be recovered by scrubbing.

It has already been proposed to employ substantially pure oxygen for the oxyhydrochlorination reaction and to recycle to the process gases from the reactor stream from which ethylene dichloride and water have been substantially removed, and to purge only a portion of the recycle stream to the atmosphere. Such cyclic processes might be expected to have reduced hydrocarbon emission because of reduced vent gas volume. Such cyclic processes, however, have not found industrial application, perhaps because it is known that processes of that kind are difficult to control and maintain under steady state conditions.

Accordingly, there is a need for an oxyhydrochlorination process for ethylene to make ethylene dichloride which will have reduced hydrocarbon emissions and which is readily controlled.

SUMMARY OF THE INVENTION

In accordance with the present invention, there is provided an improvement in the cyclic process for making ethylene dichloride by oxyhydrochlorination of ethylene involving feeding ethylene, hydrogen chloride, and substantially pure oxygen for reaction to a reaction zone containing Deacon-type catalyst, withdrawing a reactor stream comprising ethylene dichloride, water and carbon dioxide from the reaction zone, separating ethylene dichloride and water from the stream and recycling a major portion of the stream from which ethylene dichloride and water have been substantially removed to the reaction zone, wherein the oxygen and ethylene content of the recycle stream is monitored and the feed rates of ethylene, hydrogen chloride and oxygen to the reaction zone are adjusted so as to maintain in the recycle stream a concentration of ethylene within the range of from about 0.1 to 10% by volume, and a concentration of oxygen within the range of from about 0.1 to 10% by volume. For purposes of the present invention, a recycle stream from which ethylene dichloride and water have been substantially removed contains less than about 20% by volume of ethylene dichloride, and less than about 5% by volume of water, in vapor form.

We have surprisingly found that by controlling and adjusting ethylene, hydrogen chloride and oxygen feed rates to the oxyhydrochlorination reactor so as to maintain the ethylene and oxygen concentrations in the recycle stream within the above-stated limits, the recycle process can be controlled very effectively, maintenance of steady state operating conditions is facilitated, high conversions and excellent yield of the raw materials are obtained, and the amount of gas that must be vented from the system is minimized.

The balance of the stream from which ethylene dichloride and water have been substantially removed which is not recycled to the reaction zone is desirably kept at the minimum amount required to avoid build-up in the reaction zone of impurities, and, conversely, the recycle stream desirably comprises the maximum amount of gas that can be recycled consistent with maintenance of pressure within desired limits in the reaction system.

The gas which is not recycled, and is purged from the system, and may optionally be treated for recovery of additional ethylene dichloride values. The amount of purge that is required to maintain substantially constant pressure within the system can be automatically controlled by means of a back pressure control valve, for example.

BRIEF DESCRIPTION OF THE DRAWING

The drawing is a simplified flow diagram illustrating a cyclic ethylene oxyhydrochlorination process employing the improvement of the present invention.

DETAILED DESCRIPTION OF THE INVENTION, OF THE PREFERRED EMBODIMENTS AND OF THE BEST MODE CONTEMPLATED FOR ITS PRACTICE

With reference to the drawing, equipment employed includes oxyhydrochlorination reactor 1, quench tower 2, first and second condensers 3 and 4, respectively, ethylene-oxygen analyzer 5, booster compresser 6, vent stream control valve 7, vent stream washer 8 and decanter 9. These components are conventional and their design, construction, and operation are within the capabilities of a competent worker skilled in the art.

Oxyhydrochlorination reactor 1 may be a fixed bed reactor or a fluidized bed reactor containing Deacon-type catalyst, such as cupric chloride, perhaps activated by potassium chloride, on an inert support such as alumina. Such catalyst is commercially available from several suppliers. In oxyhydrochlorination reactor 1, ethylene, hydrogen chloride, and substantially pure oxygen are reacted to form a gas stream comprising ethylene dichloride, water, and by-products. As used herein, the term "substantially pure oxygen" refers to an oxygen-containing gas containing at least about 70% by volume of oxygen, and preferably at least about 90% by volume of oxygen, the balance comprising inert gas such as nitrogen. In order to dissipate heat of reaction, oxyhydrochlorination reactor 1 is preferably provided with cooling means (not shown).

Temperatures and pressures maintained in oxyhydrochlorination reactor 1 are within conventional limits. Thus, temperatures from about 370° to 530° F have been found to be satisfactory. Temperatures below about 370° F are not generally employed due to the adverse reaction rates and temperatures greater than about 530° F results in oxidation of substantial quantities of ethylene. The pressure employed is not critical, and although pressures in the reaction zone of from about 20 to 60 psig are generally employed, pressures outside this range may also be used. Of course, pressures of less than 20 psig necessitates an increased reactor size and pressures greater than 60 psig results in added equipment costs since the reactor system must be able to withstand such greater pressures.

The minimum operating pressure within the closed reaction system is determined by the temperature of the cooling medium available for use in first and second condensers 3 and 4 respectively. The pressure must be high enough to effect condensation of the ethylene dichloride product and the water by-product at the given cooling temperature. The oxyhydrochlorination reaction is strongly exothermic.

The gas stream exiting from oxyhydrochlorination reactor 1 contains ethylene dichloride and water as principal products of the reaction, together with unreacted ethylene and oxygen, unreacted hydrogen chloride, if any, and reaction by-products such as carbon dioxide, carbon monoxide and minor amounts of other chlorinated hydrocarbons such as ethyl chloride.

In subsequent operations, water and ethylene dichloride product are separated from the gas stream. The means by which this is accomplished are not critical, and the embodiments discussed herein are merely illustrative. Thus, the gas stream exiting from oxyhydrochlorination reactor 1 is first passed through quench tower 2 wherein it is contacted with an aqueous scrubbing medium at temperature in the range of from about 80° to 150° F. to cool the gas to a temperature within the range of from about 180° to 250° F., preferably from about 190° to 210° F. Scrubbing in quench tower 2 further serves to remove particulate matter, such as entrained catalyst, and to scrub out unreacted hydrogen chloride which otherwise would create corrosion problems downstream.

From quench tower 2 the gas stream is passed through first condenser 3 and, optionally, second condenser 4. These condensers are of conventional design e.g. of shell and tube-type construction, and serve to cool the gas stream to effect condensation of condensable components. Thus, in first condenser 3 the quenched gas stream is cooled to temperature within the range of from about 90° to 120° F., preferably of from about 100° to 110° F., to condense the bulk of the ethylene dichloride product and the water. The gas stream exiting first condenser 3 still containing small amounts of ethylene dichloride is further cooled in second condenser 4 to a temperature within the range of from about 80° to about 100° F., to remove additional amounts of ethylene dichloride and water, thereby providing a stream from which ethylene dichloride and water have been substantially removed. Second condenser 4 may be omitted if the temperature in first condenser 3 is reduced to that indicated above for second condenser 4.

Condensate from first and second condensers 3 and 4 is combined in decanter 9 wherein aqueous and organic phases are permitted to separate for subsequent separate withdrawal. The organic phase contains the ethylene dichloride product together with minor amounts of by-product impurities. It may be purified, as by distillation, if desired. The aqueous phase is discarded after suitable treatment to remove organic impurities contained therein.

The gas stream exiting second condenser 4 is recycled to oxyhydrochlorination reactor 1 by means of booster compressor 6 and is analyzed for ethylene and oxygen content in ethylene-oxygen analyzer 5. Ethylene-oxygen analyzer 5 comprises means for monitoring both the ethylene and the oxygen content of the recycle gas stream, preferably on continuous basis. Such means are commercially available. For example, ethylene content of the recycle stream may be determined by infrared procedure, and the oxygen content may be determined as for example by polarographic or para-magnetic oxygen analyzer. If desired, the recycled gas stream may be preheated up to the approximate reaction temperature in oxyhydrochlorination reactor 1, and preferably to a temperature of from about 300° to 400° F, prior to its introduction into that reactor.

Of course, the ethylene and oxygen content of the recycle stream can be monitored by positioning ethylene-oxygen analyzer 5 in the recycle stream line as shown in the drawing, or alternatively by positioning analyzer 5 in the vent line carrying vent gas stream, e.g. after valve 7 and before washer 8.

On start-up of operation, ethylene, substantially pure oxygen and hydrogen chloride are fed to oxyhydrochlorination reactor 1 in proportions such that there is maintained an excess over stoichiometrically required amount of about 2 to 20%, and preferably about 5 to 15% of ethylene, and about 20 to 100%, and preferably about 40 to 100%, of oxygen. Once steady state operating conditions have been achieved, feed rates of ethylene, oxygen and hydrogen chloride are adjusted such that there is maintained in the recycled gas stream, as determined by ethylene-oxygen analyzer 5, concentration of free oxygen of from about 0.1 to 10% by volume, preferably from about 2 to about 5% by volume, and concentration of ethylene of from about 0.1 to about 10% by volume, preferably from about 2 to about 5% by volume. Under maintenance of such oxygen and ethylene concentrations in the recycled gas stream the recycled gas stream will comprise in the order of from about 20 to about 50% by volume of the total feed to oxyhydrochlorination reactor 1.

Minor amounts of non-condensable inerts may be introduced into the system with the raw material feed (e.g. nitrogen with the substantially pure oxygen); and non-condensable by-products are unavoidably formed in the reaction (e.g. carbon monoxide and, principally, carbon dioxide), so that a certain amount of gas must be purged from the system. The gas so purged is taken from the recycle stream. The amount of purge is controlled by means of vent control valve 7, which in preferred embodiments is a back pressure control valve. Gas purged from the cyclic system through vent control valve 7, under steady operating conditions as above-described wherein oxygen and ethylene concentration in the recycled gas stream are controlled within the above-described limits, may contain from about 80 to 90% by volume carbon dioxide, from about 1 to about 5% by volume carbon monoxide, and less than about 5% by volume of ethylene dichloride, the balance comprising ethylene and oxygen within the above-stated limits, and minor amounts of organic by-products and water. In most preferred operation, the purge stream, prior to its discharge into the atmosphere, is subjected to further treatment to remove organics, as for example by supercooling in a coldtrap, scrubbing with suitable organic absorbents, or treatment with activated carbon. To that end, the drawing shows washer 8, which is a conventional scrubber wherein the vent gas is contacted with a gas scrubbing liquid to effect removal of organic components. Suitable scrubbing liquids include aromatic solvents such as meta-xylene. Optionally, the scrubbed vent gas stream may be further purified as by passing it through a bed of activated carbon (not shown).

Under steady state operating conditions, and when ethylene and oxygen contents of the recycled gas are controlled within the above-stated limits, the amount of gas that must be vented from the system will ordinarily amount to no more than about 2 to 20% by volume, more usually between about 5 to about 10% by volume of the stream withdrawn from the cooling condenser (5) (condensers 3 and 4 in the drawing) from which ethylene dichloride and water have been substantially removed. Thus, ordinarily from about 80 to about 98% by volume, and more usually from about 90 to about 95% by volume of the stream from which ethylene dichloride and water have been substantially removed, is recycled to the reaction zone. This means that there is effected an about 80 to 98 percent reduction in the total volume of gas vented to the atmosphere, as compared to conventional single-pass oxyhydrochlorination processes. This in itself represents a substantial reduction in the amount of pollutants discharged into the atmosphere. Moreover, however, since in the cyclic process the vent gas stream is of relatively much smaller volume than that of a conventional single pass oxyhydrochlorination process, it is economically feasible to further treat this reduced volume of vent gas to effect further reduction of organic contaminants therein, as by scrubbing it in the manner above-described, so that in overall operation the amount of pollutants discharged into the atmosphere by the cyclic oxyhydrochlorination process embodying the improvement of our invention need only be a small fraction of that discharged in a conventional single pass process.

The closely controlled cyclic process of the present invention compares very favorably with conventional single pass processes with respect to yields, as is indicated below in Table I.

TABLE I

| Starting Material | % Yield Single Pass Process | % Yield Recycle Process |
|---|---|---|
| Hydrogen Chloride | 99.9 | 99.9 |
| Ethylene | 90 | 95 |
| Oxygen | 55 | 65 |

While these yields are subject to considerable variation depending upon process conditions, type of catalyst and efficiency of the apparatus employed, the above data are based on conditions believed to be typical and comparable, and are indicative of the high yields which may be obtained by the improved process of our invention.

The following example, wherein parts are by weight unless otherwise indicated, further illustrate the present invention and sets forth the best mode presently contemplated for its practice.

EXAMPLE

Apparatus employed is substantially as described above. The oxyhydrochlorination reactor is a fluidized bed reactor wherein superficial gas velocity is maintained at about 1.2 feet per second. Temperature in the reactor is maintained at about 448° F. and pressure is about 44 psig. The reactants are fed to the reactor at the following rates: hydrogen chloride, 4,536 parts per hour; ethylene, 1,818 parts per hour; oxygen (in the form of pure oxygen), 1,320 parts per hour.

The exit stream from the reactor is fed to the quench tower to which water is fed at the rate of 1,800 parts per hour at temperature of about 90° F., and water is withdrawn at the rate of 1,633 parts per hour. In the quench tower the gas stream is cooled to about 200° F.

The quenched gas stream is then passed serially through two condensers wherein it is cooled in the first condenser to temperature of about 100° F. and is further cooled in the second condenser to about 95° F. Condensate is collected, and aqueous and organic phases are permitted to separate. Organics are collected at the rate of 6,349 parts per hour; water at the rate of 1,106 parts per hour. The composition of the organic product stream is as follows:

|  | % By Weight |
|---|---|
| ethylene | .12 |
| vinyl chloride | .006 |
| ethyl chloride | .049 |
| methylene chloride | .002 |
| trans-ethylene dichloride | .03 |
| cis-ethylene dichloride | .101 |
| ethylene dichloride | 98.509 |
| carbon tetrachloride | .14 |
| trichloroethylene | .09 |
| trichloroethane | .499 |
| perchloroethylene | .098 |
| tetrachloroethane | .13 |
| pentachloroethane | .026 |
| water | .20 |

Total purge gas vented from the system amounts to 376 parts per hour. Total feed to the reactor amounts to 13,921 parts per hour, of which 6,258 parts per hour is accounted for by the recycle stream.

The vent stream purged from the system prior to discharge is passed through a refrigerated condenser and has the following composition by volume: oxygen, 7.96%; nitrogen and carbon dioxide combined, 87.6%; carbon monoxide, 1.79%; ethylene, 1.99%; ethane, 0.1%; and ethylene dichloride, 0.54%. The vent gas stream prior to passage through the refrigerated condenser contained about 5 to 6% by volume of ethylene dichloride. Ethylene conversion is 99.3% with ethylene yield of 98.1%; oxygen conversion is 98% with oxygen yield at 77.7%.

Since various changes and modifications may be made in the invention without departing from the spirit and essential characteristics, it is intended that all matter contained in the above description shall be interpreted as illustrative only.

We claim:

1. In a process for producing ethylene dichloride by the oxyhydrochlorination of ethylene wherein (1) ethylene, hydrogen chloride and substantially pure oxygen are fed to a reaction zone containing a Deacon-type catalyst and reacted therein to form ethylene dichloride, (2) a product stream containing ethylene dichloride, water, carbon dioxide, carbon monoxide and unreacted ethylene and oxygen is withdrawn from the reaction zone, and (3) ethylene dichloride and water are removed from the product stream and a major portion of the product stream is thereafter recycled to the reaction zone as a recycle stream, the improvement which comprises: monitoring the oxygen and ethylene content of the recycle stream and adjusting the feed rates of ethylene, hydrogen chloride and oxygen to the reaction zone so as to maintain in the recycle stream a concentration of ethylene within the range of from about 0.1 to 10% by volume, and a concentration of oxygen within the range of from about 0.1 to 10% by volume.

2. The process of claim 1 wherein the portion of the product stream which is not recycled to the reaction zone is released as a purge stream.

3. The process of claim 2 which includes the additional step of monitoring the pressure of the recycle stream and adjusting the flow of the purge stream so as to maintain a substantially constant recycle stream pressure.

4. The process of claim 3 wherein the recycle stream comprises from about 85 to 95% by volume of the product stream after removal of ethylene dichloride and water therefrom.

5. The process of claim 3 which includes the additional step of recovering additional ethylene dichloride values from said purge stream.

6. The process of claim 1 wherein said recycle stream is heated to a temperature of from about 300° to 400° F. prior to introducing said stream into the reaction zone.

7. The process of claim 3 when said recycle stream pressure is maintained within the range of from about 40 to 60 psig.

* * * * *

Disclaimer 4,071,572.—*Wayne S. Amato,* Syracuse; *Bhaskar Bandyopadhyay,* Camillus; *Robert Herbert Fitch,* Syracuse; and *Bruce Edward Kurtz,* Marcellus, all of N.Y. CYCLIC ETHYLENE OXYHYDROCHLORINATION PROCESS WITH REDUCED HYDROCARBON EMISSIONS. Patent dated Jan. 31, 1978. Disclaimer filed Dec. 8, 1983, by the assignee, *The United States of America as represented by the Administrator of the U.S. Environmental Protection Agency.*

Hereby enters this disclaimer to claim 1 of said patent.

[*Official Gazette March 27, 1984.*]